(12) United States Patent
Mittal et al.

(10) Patent No.: US 8,853,411 B2
(45) Date of Patent: Oct. 7, 2014

(54) PROCESS FOR THE PREPARATION OF DEXLANSOPRAZOLE

(75) Inventors: Anu Mittal, Kurukshetra (IN); Anmol Kumar Ray, Jaipur (IN); Mahavir Singh Khanna, New Delhi (IN); Rajesh Kumar Thaper, Jammu (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 115 days.

(21) Appl. No.: 13/638,399

(22) PCT Filed: Mar. 29, 2011

(86) PCT No.: PCT/IB2011/051345
§ 371 (c)(1),
(2), (4) Date: Feb. 12, 2013

(87) PCT Pub. No.: WO2011/121548
PCT Pub. Date: Oct. 6, 2011

(65) Prior Publication Data
US 2013/0204002 A1    Aug. 8, 2013

(30) Foreign Application Priority Data
Mar. 31, 2010  (IN) .............................. 796/DEL/2010

(51) Int. Cl.
*C07D 401/12*    (2006.01)
(52) U.S. Cl.
USPC ...................................................... 546/273.7
(58) Field of Classification Search
CPC ...................................................... C07D 401/12
USPC ...................................................... 546/273.7
See application file for complete search history.

(56) References Cited

U.S. PATENT DOCUMENTS

| | | | |
|---|---|---|---|
| 6,462,058 B1 | 10/2002 | Fujishima et al. | 514/338 |
| 7,271,182 B2 | 9/2007 | Kamiyama et al. | 514/338 |
| 7,285,668 B2 | 10/2007 | Hashimoto et al. | 546/273.7 |
| 8,198,455 B2 | 6/2012 | Attolino et al. | 546/273.7 |
| 2004/0010151 A1 | 1/2004 | Finkelstein et al. | 548/257 |
| 2007/0004779 A1 | 1/2007 | Hashimoto et al. | 514/338 |

FOREIGN PATENT DOCUMENTS

WO    WO 2009/117489    9/2009    ........... C07D 403/12

*Primary Examiner* — Patricia L Morris

(57) ABSTRACT

The present invention relates to a process for the preparation of crystalline dexlansoprazole.

14 Claims, 6 Drawing Sheets

FIGURE 1A: TABLE OF VALUES FOR THE XRPD PATTERN DEPICTED IN FIGURE 1

| Pos [°2Th] | d-spacing [Å] | Rel. Int [%] |
|---|---|---|
| 7.55 | 11.71 | 61.09 |
| 10.44 | 8.47 | 4.38 |
| 11.10 | 7.97 | 6.99 |
| 13.06 | 6.78 | 100.00 |
| 13.56 | 6.53 | 25.70 |
| 15.15 | 5.85 | 28.71 |
| 15.44 | 5.74 | 91.08 |
| 17.30 | 5.12 | 14.69 |
| 18.27 | 4.86 | 11.33 |
| 18.55 | 4.78 | 7.90 |
| 20.02 | 4.44 | 35.92 |
| 20.18 | 4.40 | 14.59 |
| 20.98 | 4.23 | 15.24 |
| 21.32 | 4.17 | 32.47 |
| 21.49 | 4.14 | 69.58 |
| 21.69 | 4.10 | 89.49 |
| 22.55 | 3.94 | 37.69 |
| 22.76 | 3.91 | 27.01 |
| 23.07 | 3.85 | 10.12 |
| 24.06 | 3.70 | 65.59 |
| 25.33 | 3.52 | 9.71 |
| 26.11 | 3.41 | 49.44 |
| 26.30 | 3.39 | 26.30 |
| 26.90 | 3.31 | 7.03 |
| 27.31 | 3.26 | 21.43 |
| 28.64 | 3.12 | 42.39 |
| 30.03 | 2.98 | 8.87 |
| 30.41 | 2.94 | 20.37 |
| 31.18 | 2.87 | 13.03 |
| 31.48 | 2.84 | 10.40 |
| 32.50 | 2.75 | 10.47 |
| 33.04 | 2.71 | 6.82 |
| 34.32 | 2.61 | 7.75 |
| 36.20 | 2.48 | 7.90 |
| 37.23 | 2.41 | 6.07 |
| 37.75 | 2.38 | 5.81 |
| 39.21 | 2.30 | 7.33 |

FIGURE 2A: TABLE OF VALUES FOR THE XRPD PATTERN DEPICTED IN FIGURE 2

| Pos [°2Th] | d-spacing [Å] | Rel. Int [%] |
|---|---|---|
| 7.55 | 11.70 | 59.77 |
| 10.43 | 8.48 | 4.29 |
| 11.10 | 7.97 | 7.18 |
| 13.06 | 6.78 | 100.00 |
| 13.56 | 6.53 | 23.81 |
| 15.15 | 5.85 | 30.81 |
| 15.44 | 5.74 | 92.41 |
| 17.30 | 5.13 | 14.65 |
| 18.27 | 4.86 | 11.06 |
| 18.55 | 4.78 | 8.24 |
| 20.02 | 4.43 | 34.63 |
| 20.18 | 4.40 | 14.43 |
| 20.96 | 4.24 | 15.60 |
| 21.31 | 4.17 | 27.98 |
| 21.49 | 4.13 | 64.76 |
| 21.70 | 4.10 | 83.16 |
| 22.55 | 3.94 | 35.40 |
| 22.76 | 3.91 | 28.88 |
| 23.07 | 3.85 | 9.42 |
| 24.06 | 3.70 | 59.96 |
| 25.31 | 3.52 | 10.25 |
| 26.12 | 3.41 | 46.72 |
| 26.29 | 3.39 | 26.69 |
| 26.88 | 3.32 | 6.57 |
| 27.32 | 3.26 | 20.91 |
| 28.64 | 3.12 | 39.61 |
| 30.03 | 2.98 | 8.93 |
| 30.41 | 2.94 | 19.66 |
| 31.17 | 2.87 | 11.87 |
| 31.49 | 2.84 | 10.24 |
| 32.50 | 2.75 | 10.18 |
| 33.04 | 2.71 | 6.30 |
| 34.31 | 2.61 | 7.99 |
| 36.20 | 2.48 | 7.76 |
| 37.24 | 2.41 | 5.41 |
| 37.74 | 2.38 | 5.77 |
| 39.20 | 2.30 | 6.89 |

FIGURE 3A: TABLE OF VALUES FOR THE XRPD PATTERN DEPICTED IN FIGURE 3

| Pos [°2Th] | d-spacing [Å] | Rel. Int [%] |
| --- | --- | --- |
| 7.57 | 11.68 | 68.79 |
| 10.45 | 8.47 | 4.36 |
| 11.10 | 7.97 | 6.74 |
| 13.07 | 6.77 | 100.00 |
| 13.57 | 6.53 | 23.12 |
| 15.17 | 5.84 | 32.89 |
| 15.45 | 5.74 | 96.88 |
| 17.31 | 5.12 | 15.07 |
| 18.27 | 4.85 | 11.06 |
| 18.55 | 4.78 | 8.06 |
| 20.03 | 4.43 | 36.15 |
| 20.18 | 4.40 | 15.26 |
| 20.98 | 4.23 | 14.31 |
| 21.49 | 4.13 | 66.87 |
| 21.71 | 4.09 | 90.82 |
| 22.56 | 3.94 | 36.62 |
| 22.79 | 3.90 | 25.11 |
| 23.09 | 3.85 | 9.32 |
| 24.07 | 3.70 | 59.90 |
| 25.32 | 3.52 | 10.82 |
| 26.12 | 3.41 | 47.01 |
| 26.31 | 3.39 | 26.36 |
| 26.88 | 3.32 | 6.54 |
| 27.32 | 3.26 | 20.50 |
| 28.64 | 3.12 | 39.62 |
| 30.02 | 2.98 | 8.46 |
| 30.41 | 2.94 | 19.30 |
| 31.17 | 2.87 | 11.15 |
| 31.47 | 2.84 | 11.46 |
| 32.51 | 2.75 | 9.95 |
| 33.03 | 2.71 | 6.25 |
| 34.40 | 2.61 | 6.51 |
| 36.22 | 2.48 | 7.92 |
| 37.24 | 2.41 | 5.56 |
| 37.75 | 2.38 | 5.53 |
| 39.20 | 2.30 | 6.97 |

PROCESS FOR THE PREPARATION OF DEXLANSOPRAZOLE

FIELD OF THE INVENTION

The present invention relates to a process for the preparation of crystalline dexlansoprazole.

BACKGROUND OF THE INVENTION

Dexlansoprazole is chemically described as 2-[(R)-{[3-methyl-4-(2,2,2-trifluoroethoxy)pyridin-2-yl]methyl}sulfinyl]-1H-benzimidazole as represented by Formula I.

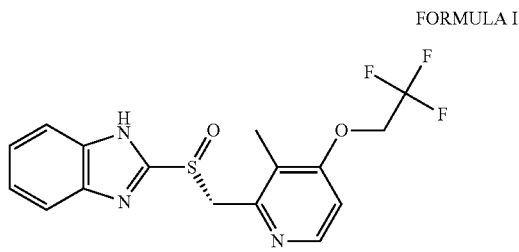

FORMULA I

Dexlansoprazole is reportedly useful for healing of all grades of erosive esophagitis (EE) for up to 8 weeks, to maintain healing of EE for up to 6 months and for the treatment of heartburn associated with non-erosive gastroesophageal reflux disease (GERD) for 4 weeks.

U.S. Pat. Nos. 6,462,058 and 7,285,668 and U.S. Publication No. 2007/0004779 describe processes for preparing crystalline forms of dexlansoprazole and its hydrates. PCT Publication No. WO 2009/117489 describes processes for the preparation of amorphous dexlansoprazole.

U.S. Pat. No. 7,271,182 discloses the formation of alkali and alkaline earth metal salts—such as sodium, magnesium, lithium, potassium, calcium, and barium—of dexlansoprazole, by reacting dexlansoprazole with a metal hydroxide, a metal alkoxide or a metal amide.

SUMMARY OF THE INVENTION

The present inventors have found that certain salts of dexlansoprazole can be converted into crystalline dexlansoprazole. By employing the present invention, crystalline dexlansoprazole can also be obtained as a chirally and chemically pure material in a consistent manner. Thus, the present invention provides a simple, efficient and industrially preferable process for the preparation of crystalline dexlansoprazole.

BRIEF DESCRIPTION OF THE DRAWINGS

FIG. 1A provides the peak values for the XRPD pattern depicted in FIG. 1.

FIG. 2A provides the peak values for the XRPD pattern depicted in FIG. 2.

FIG. 3A provides the peak values for the XRPD pattern depicted in FIG. 3.

DETAILED DESCRIPTION OF THE INVENTION

Figure 1:
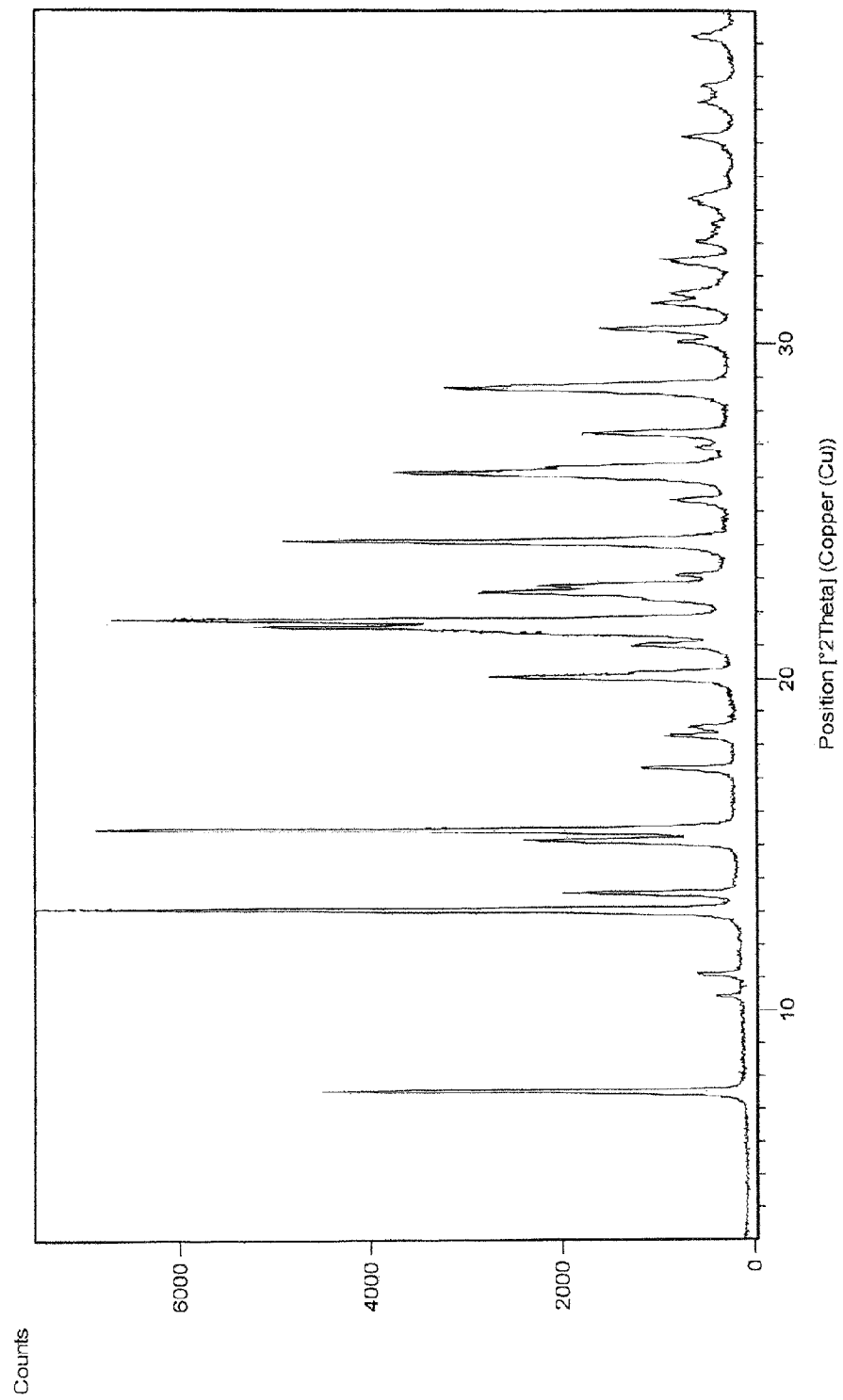
FIG. 1 depicts the X-ray powder diffraction pattern (XRPD) of crystalline dexlansoprazole obtained according to Example 1.
Figure 2:
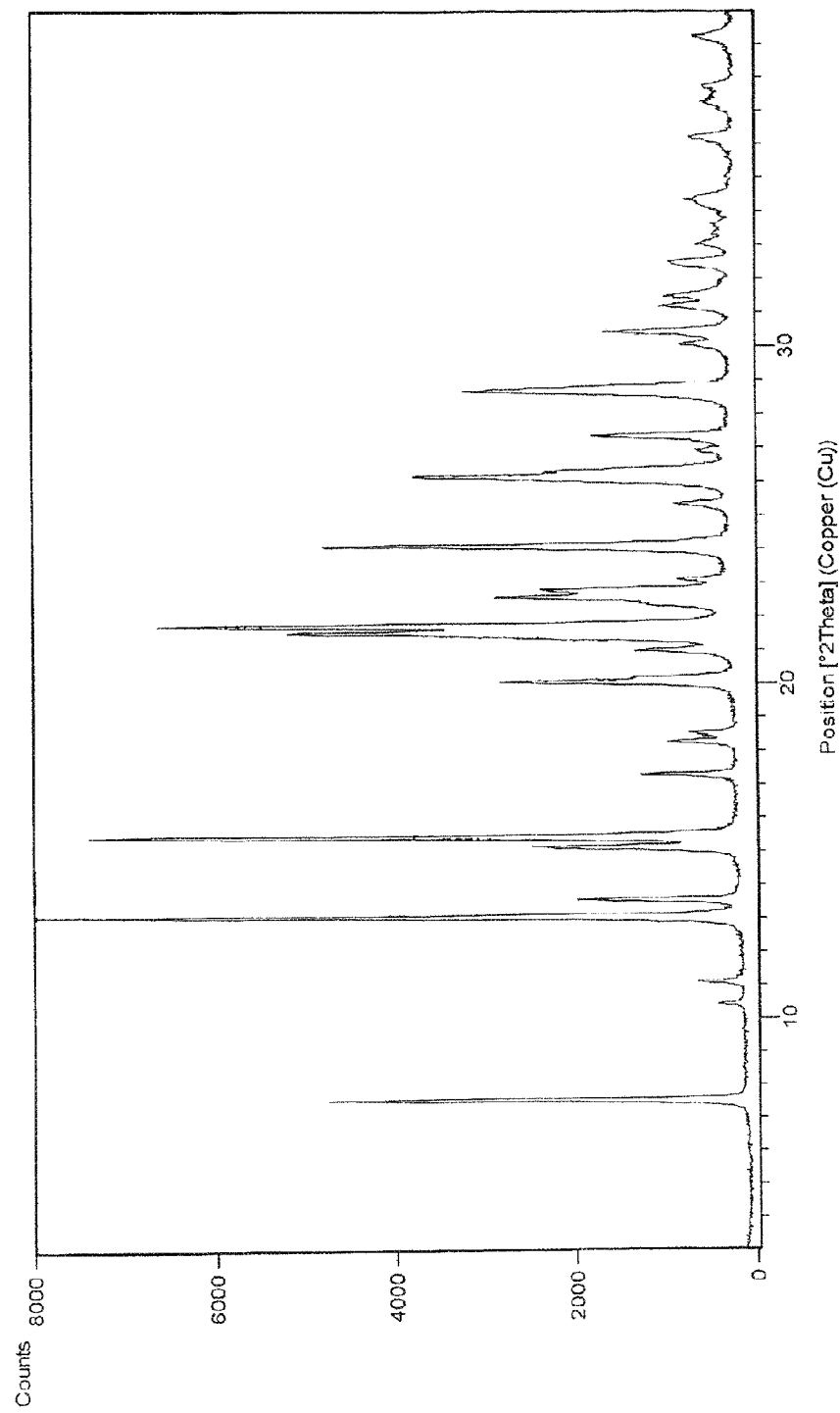
FIG. 2 depicts the X-ray powder diffraction pattern (XRPD) of crystalline dexlansoprazole obtained according to Example 2.
Figure 3:
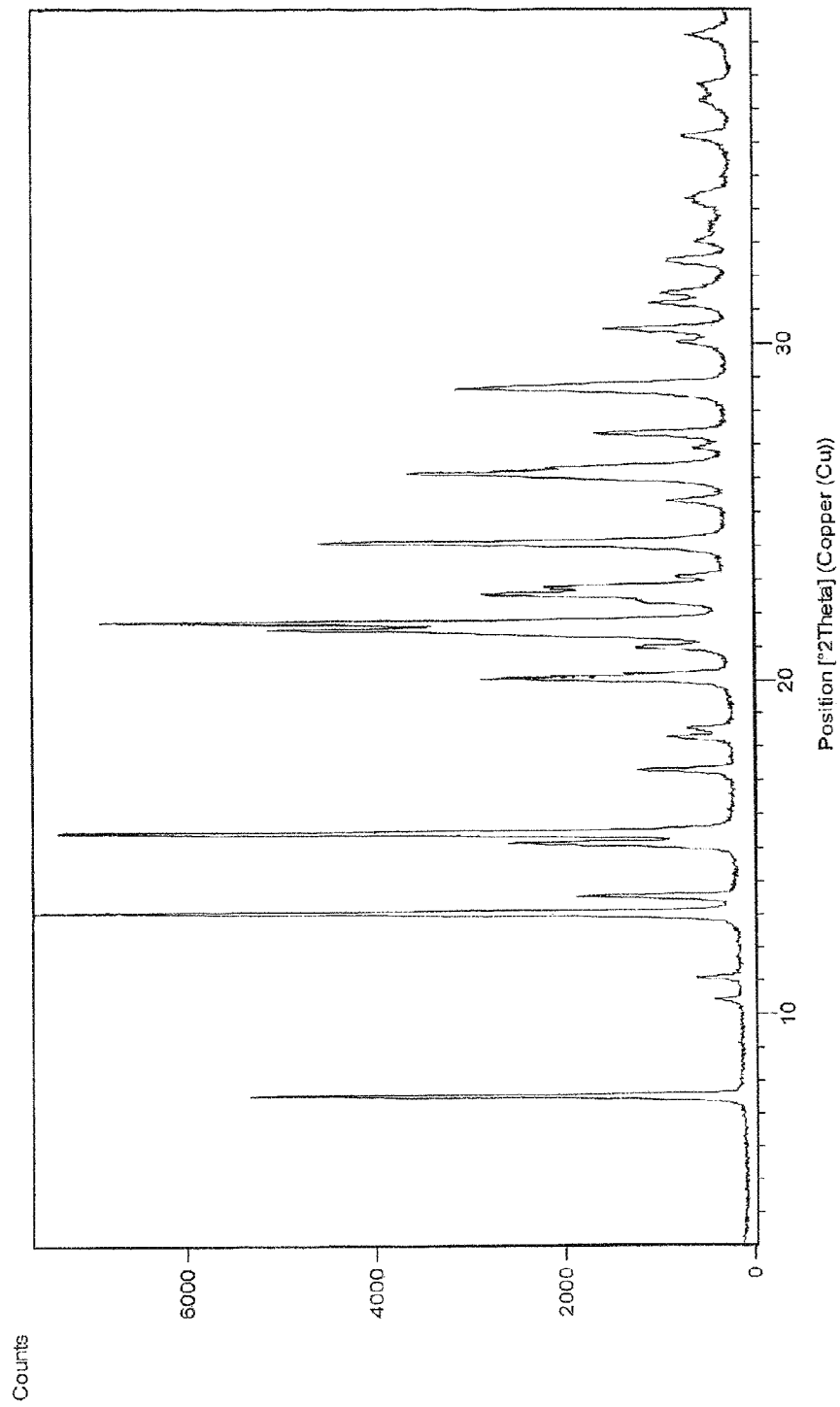
FIG. 3 depicts the X-ray powder diffraction pattern (XRPD) of crystalline dexlansoprazole obtained according to Example 3.

One aspect of the present invention provides a process for the preparation of crystalline dexlansoprazole, which comprises the steps of:

a) treating a salt of dexlansoprazole with an agent capable of liberating dexlansoprazole as a free base in the presence of a solvent;

b) treating the dexlansoprazole obtained in step a) with a solvent selected from the group consisting of water, halogenated hydrocarbon, $C_{1-3}$ alkanol, ether and a mixture thereof; and c) isolating crystalline dexlansoprazole from the mixture.

The salt of dexlansoprazole used as a starting material may be in any form and prepared according to the methods described in U.S. Pat. No. 7,271,182. The salt may be for example, alkali metal salt or alkaline earth metal salt, for example, sodium salt of dexlansoprazole. The salt of dexlansoprazole is treated with an agent capable of liberating dexlansoprazole as a free base in the presence of a solvent. The agent capable of liberating dexlansoprazole as a free base may be an amine salt, for example, ammonium halide, or a hydrogen sulfate, for example, sodium or potassium hydrogen sulfate, or both. The solvent may be a water miscible solvent, for example, acetone, $C_{1-3}$ alkanol, dioxane, tetrahydrofuran, dimethylformamide, acetonitrile, dimethylsulfoxide or a mixture thereof. The liberation of dexlansoprazole as a free base may be effected by stirring the reaction mixture. The reaction mixture may be treated with ammonia, for example aqueous ammonia or an alkyl amine in the presence of a ketone solvent, for example, acetone to remove 2-({[3-methyl-4-(2,2,2-trifluoroethoxy)pyridin-2-yl]methyl}sulfonyl)-1H-benzimidazole impurity (sulfone impurity). The dexlansoprazole obtained as a free base may optionally be isolated by solvent removal. The dexlansoprazole is treated with a solvent selected from the group consisting of water, halogenated hydrocarbon, $C_{1-3}$ alkanol, ether, and a mixture thereof. The solvent may be, for example, dichloromethane, methanol, methyl t-butyl ether, diisopropyl ether, or a mixture thereof. The treatment with the solvent may be carried out at a temperature of about −30° C. to about 60° C., for example, about 15° C. to about 45° C. The crystalline dexlansoprazole may be isolated by filtration, distillation, decantation, vacuum drying, evaporation, or a combination thereof.

Crystalline dexlansoprazole prepared by the present invention has a purity of more than about 99.0%, for example more than about 99.4% and chiral purity of more than about 99.9% and is substantially free from sulfone impurity. For example, the crystalline dexlansoprazole has a sulfone impurity not more than about 0.1%.

XRPD of the samples were determined by using Panalytical X'Pert Pro X-Ray Powder Diffractometer in the range 3-40 degree 2 theta and under tube voltage and current of 45 Kv and 40 mA respectively. Copper radiation of wavelength 1.54 angstrom and Xceletor detector was used.

While the present invention has been described in terms of its specific embodiments, certain modifications and equivalents will be apparent to those skilled in the art and are intended to be included within the scope of the present invention.

EXAMPLES

Example 1

Preparation of Crystalline Dexlansoprazole

A mixture of acetone (30 mL) and dexlasoprazole sodium (10 g; sulfone impurity content: 6%) was stirred at 20° C. to 25° C. and filtered through 0.45μ filter. De-ionized water (10 mL) was added to the filtered solution at 20° C. to 25° C., followed by addition of aqueous sodium hydrogen sulfate (2.5 g of sodium hydrogen sulfate in 7 mL of water) drop-wise till pH 7.3 was reached. The mixture was stirred for 10 to 15 minutes, followed by the addition of de-ionized water (50 mL) and stirred for further 1 hour at 20° C. to 25° C. The mixture was filtered under vacuum, washed with de-ionized water (10 mL), followed by addition of acetone (30 mL) and 6% aqueous ammonia solution (0.5 mL; 6%) to attain a pH of 9.5. De-ionized water (60 mL) was added to the mixture, stirred for 1 hour at 20° C. to 25° C., filtered under vacuum and washed with de-ionized water (10 mL), followed by the addition of de-ionized water (30 mL) and dichloromethane (60 mL). The mixture was stirred and then allowed to settle, and the organic layer was separated. Dichloromethane was recovered under vacuum at 35° C. to 40° C. to obtain 10 to 15 mL of reaction mixture. Diisopropyl ether (150 mL) was added drop-wise to the reaction mixture, stirred for 1 hour at 20° C. to 25° C., filtered under vacuum, washed with diisopropyl ether (10 mL) and dried under vacuum at 20° C. to 25° C. for 8 hours to 10 hours to obtain the title compound.
Yield: 71.27%
Chiral purity: 99.9%
Chromatographic purity: 99.78%
Sulfone impurity content: not detectable
Moisture content: 0.12%

Example 2

Preparation of Crystalline Dexlansoprazole

A mixture of acetone (100 mL) and dexlasoprazole sodium (20 g) was stirred at 20° C. to 30° C. and filtered through 0.45μ filter. Ammonium chloride solution (40 g of ammonium chloride in 120 mL of water) was added to the filtered solution at 20° C. to 25° C. accompanied by stirring, followed by addition of 5% aqueous potassium hydrogen sulfate drop-wise to attain a pH of 6.99. The mixture was stirred for 45 minutes and filtered under vacuum. Water (180 mL) was added slowly to the filtrate at 20° C. to 25° C. and stirred for 45 minutes. 6% Aqueous ammonia solution (0.5 mL; 6%) was added drop-wise to attain a pH of 9, filtered under vacuum and washed with acetone/de-ionized water (1/2, 150 mL) and dried under vacuum in air for 2 hours. 8.5 g of the solid was stirred with dichloromethane (100 mL) and de-ionized water (75 mL), and the organic layer was separated. The solvent was recovered under vacuum at 35° C. to 40° C. to obtain 10 to 15 mL of reaction mixture. Methanol (25 mL) was added to the reaction mixture and the solvent was evaporated under vacuum at 35° C. to 40° C. to obtain 10 to 15 mL of reaction mixture. Diisopropyl ether (125 mL) was added to the reaction mixture drop-wise at 20° C. to 25° C., stirred for 1 hour at 20° C. to 25° C., filtered under vacuum. The solid was washed with diisopropyl ether (25 mL) and dried under vacuum at 30° C. to 35° C. for 4 hours using calcium chloride as a drying agent to obtain the title compound.
Yield: 6.5 g
Chiral purity: 100%
Chromatographic purity: 99.45%
Sulfone impurity content: not detectable
Moisture content: 0.1%

Example 3

Preparation of Crystalline Dexlansoprazole

A mixture of acetone (100 mL) and dexlasoprazole sodium (20 g) was stirred at 20° C. to 30° C. and filtered through 0.45μ filter. Ammonium chloride solution (40 g of ammonium chloride in 120 mL of water) was added to the filtered solution at 20° C. to 25° C. accompanied by stirring, followed by addition of 5% aqueous potassium hydrogen sulfate drop-wise to attain a pH of 6.99. The mixture was stirred for 45 minutes and filtered under vacuum. Water (180 mL) was added slowly to the filtrate at 20° C. to 25° C. and stirred for 45 minutes. 6% Aqueous ammonia solution (0.5 mL; 6%) was added drop-wise to attain a pH of 9, filtered under vacuum and washed with acetone/de-ionized water (1/2, 150 mL) and dried under vacuum in air for 2 hours. 7.5 g of the solid was stirred with dichloromethane (100 mL) and de-ionized water (75 mL) and the organic layer was separated. The solvent was recovered under vacuum at 35° C. to 40° C. to obtain 8 to 12 mL of reaction mixture. Methyl t-butyl ether (110 mL) was added drop-wise to the reaction mixture at 20° C. to 25° C., stirred for 1 hour at 20° C. to 25° C. and filtered under vacuum. The solid was washed with diisopropyl ether (20 mL) and dried under vacuum at 30° C. to 35° C. for 4 hours using calcium chloride as a drying agent to obtain the title compound.
Yield: 4 g
Chiral purity: 100%
Chromatographic purity: 99.4%
Sulfone impurity content: not detectable
Moisture content: 0.1%

We claim:
1. A process for the preparation of crystalline dexlansoprazole, the process comprising the steps of:
   a) treating a salt of dexlansoprazole with an agent capable of liberating dexlansoprazole as a free base in the presence of a solvent;
   b) treating the dexlansoprazole obtained in step a) with a solvent selected from the group consisting of water, halogenated hydrocarbon, C1-3 alkanol, ether and a mixture thereof; and
   c) isolating crystalline dexlansoprazole from the mixture thereof.
2. A process according to claim 1, wherein the agent capable of liberating dexlansoprazole is amine salt or hydrogen sulfate.
3. A process according to claim 2, wherein the hydrogen sulfate is sodium hydrogen sulfate, potassium hydrogen sulfate or both.
4. A process according to claim 1, wherein the salt of dexlansoprazole is alkali metal salt or alkaline earth metal salt.
5. A process according to claim 4, wherein the alkali metal salt of dexlansoprazole is sodium salt.
6. A process according to claim 1, wherein the solvent used in step a) is a water miscible solvent.
7. A process according to claim 6, wherein the water miscible solvent is acetone, C1-3 alkanol, dioxane, tetrahydrofuran, dimethylformamide, acetonitrile, dimethylsulfoxide or a mixture thereof.
8. A process according to claim 1, wherein the halogenated hydrocarbon solvent used in step b) is dichloromethane.

9. A process according to claim 1, wherein the C1-3 alkanol solvent used in step b) is methanol.

10. A process according to claim 1, wherein the ether solvent used in step b) is methyl t-butyl ether, diisopropyl ether or a mixture thereof.

11. A process according to claim 1, wherein crystalline dexlansoprazole obtained in step c) has chromatographic purity of at least 99%.

12. A process according to claim 1, wherein crystalline dexlansoprazole obtained in step c) has sulfone impurity of not more than 0.1%.

13. A process according to claim 1, wherein crystalline dexlansoprazole obtained in step c) has water content of not more than 0.2%.

14. A process according to claim 1, wherein crystalline dexlansoprazole obtained in step c) has sulfone impurity of not more than 0.1% and water content not more than 0.2%.

\* \* \* \* \*

UNITED STATES PATENT AND TRADEMARK OFFICE
CERTIFICATE OF CORRECTION

| | | |
|---|---|---|
| PATENT NO. | : 8,853,411 B2 | Page 1 of 1 |
| APPLICATION NO. | : 13/638399 | |
| DATED | : October 7, 2014 | |
| INVENTOR(S) | : Mittal et al. | |

It is certified that error appears in the above-identified patent and that said Letters Patent is hereby corrected as shown below:

In the specification

COLUMN 2, LINES 14 and 42:

"$C_{1-3}$alkanol, ether"     should read     -- $C_{1-3}$ alkanol, ether --

In the claims

COLUMN 4, CLAIM 1, LINE 45:

"C1-3 alkanol, ether"     should read     -- $C_{1-3}$ alkanol, ether --

COLUMN 4, CLAIM 7, LINE 63:

"C1-3 alkanol, dioxane,"     should read     -- $C_{1-3}$ alkanol, dioxane, --

COLUMN 5, CLAIM 9, LINE 1:

"C1-3 alkanol"     should read     -- $C_{1-3}$ alkanol --

Signed and Sealed this
Sixth Day of October, 2015

Michelle K. Lee
*Director of the United States Patent and Trademark Office*